United States Patent
Carlavan

(10) Patent No.: US 10,760,129 B2
(45) Date of Patent: Sep. 1, 2020

(54) TH17 DIFFERENTIATION MARKERS FOR ACNE AND USES THEREOF

(71) Applicant: GALDERMA RESEARCH & DEVELOPMENT, Biot (FR)

(72) Inventor: Isabelle Carlavan, Grasse (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 539 days.

(21) Appl. No.: 15/136,626

(22) Filed: Apr. 22, 2016

(65) Prior Publication Data

US 2016/0237503 A1 Aug. 18, 2016

Related U.S. Application Data

(62) Division of application No. 14/129,733, filed as application No. PCT/EP2012/062257 on Jun. 25, 2012, now abandoned.

(60) Provisional application No. 61/501,363, filed on Jun. 27, 2011.

(51) Int. Cl.

| | |
|---|---|
| C12Q 1/6883 | (2018.01) |
| G01N 33/50 | (2006.01) |
| H01R 31/02 | (2006.01) |
| G01N 33/569 | (2006.01) |
| G01N 33/68 | (2006.01) |
| H01R 13/66 | (2006.01) |

(52) U.S. Cl.
CPC ......... *C12Q 1/6883* (2013.01); *G01N 33/505* (2013.01); *G01N 33/56972* (2013.01); *G01N 33/6869* (2013.01); *H01R 31/02* (2013.01); *C12Q 2600/158* (2013.01); *H01R 13/6675* (2013.01)

(58) Field of Classification Search
CPC . C12Q 1/6883; C12Q 2600/158; A61P 17/10; G01N 33/505; G01N 33/6869
See application file for complete search history.

(56) References Cited

U.S. PATENT DOCUMENTS

| | | |
|---|---|---|
| 5,536,657 A | 7/1996 | Chua et al. |
| 6,054,487 A | 4/2000 | Sekut et al. |
| 2002/0102232 A1 | 8/2002 | Chang et al. |
| 2005/0101581 A1 | 5/2005 | Reading et al. |
| 2006/0275282 A1 | 12/2006 | Moore et al. |
| 2007/0065415 A1 | 3/2007 | Kleinsek et al. |
| 2007/0081975 A1 | 4/2007 | Novick et al. |
| 2007/0269765 A1 | 11/2007 | Danger et al. |
| 2008/0171715 A1 | 7/2008 | Brown et al. |
| 2009/0300776 A1 | 12/2009 | Lecron et al. |
| 2010/0166784 A1 | 7/2010 | Murphy et al. |
| 2010/0190710 A1 | 7/2010 | Chemtob et al. |
| 2010/0292153 A1 | 11/2010 | Strober |
| 2010/0324109 A1 | 12/2010 | Saurat |
| 2011/0212935 A1 | 9/2011 | Frincke |
| 2012/0142544 A1 | 6/2012 | Hare et al. |
| 2013/0177979 A1 | 7/2013 | Turkson |

FOREIGN PATENT DOCUMENTS

| | | |
|---|---|---|
| WO | WO-02/089791 A2 | 11/2002 |
| WO | 2005/108616 A1 | 11/2005 |
| WO | 2007/077257 A2 | 7/2007 |
| WO | WO-2007/077257 A2 | 7/2007 |
| WO | WO-2010/066641 A1 | 6/2010 |
| WO | WO-2011/007183 A2 | 1/2011 |

OTHER PUBLICATIONS

Fan, J. et al., Retinoic Acid Receptor-Related Orphan Receptors: Critical Roles in Tumorigenesis, Frontiers in Immunol., vol. 9:1187, pp. 1-10 (Year: 2018).*
Trevino, V. et al., DNA Microarrays: a Powerful Genomic Tool for Biomedical and Clinical Research, Mol. Meth., vol. 13, pp. 527-541 (Year: 2007).*
Kistowska, M. et al., Propionibacterium acnes Promotes Th17 and TH17/Th1 Responses in Acne Patients, J. Invest. Dermatol., vol. 134, pp. 110-118 (Year: 2015).*
International Search Report and Written Opinion dated Aug. 20, 2012 by the European Patent Office as the International Searching Authority in corresponding International Patent Application No. PCT/EP2012/062257, 15 pages.
Abromson-Leeman, et al., "Encephalitogenic T cells that stably express both T-bet and RORyt consistently produce IFNy but have a spectrum of IL-17 profiles," Journal of Neuroimmunology, Elsevier Science Publishers, vol. 215, No. 1-12, Oct. 30, 2009, pp. 10-24. AGA Abstracts, p. A-253.
Chung, et al., "Critical Regulation of Early Th17 Cell Differentiation by Interleukin-1 Signaling," Immunity, vol. 30, No. 4, Apr. 1, 2009, pp. 576-587.
He, et al., "Down-Regulation of the Orphan Nuclear Receptor RORyt Is Essential for T Lymphocyte Maturation," The Journal of Immunology, The American Association of Immunilogists, vol. 164, No. 11, Jun. 1, 2000, pp. 5668-5674.
Hendrick, et al., "CCR6 is required of IL-23-induced psoriasis-like inflammation in mice," Journal of Clinical Investigation, vol. 119, No. 8, Aug. 3, 2009, pp. 2317-2329.
Leppkes, et al., "RORy-Expressing Th17 Cells Induce Murine Chronic Intestinal Inflammation via Redundant Effects of IL-17A and IL-17F," Gastroenterolovy, Elsevier, vol. 136, No. 1, pp. 257-267.
Martinez, et al., "Regulation and Function of Proinflammatory TH17 Cells," Annals of the New York Academy of Sciences, vol. 1143, No. 1, Nov. 1, 2008, pp. 188-211.

(Continued)

*Primary Examiner* — Teresa E Strzelecka
(74) *Attorney, Agent, or Firm* — Foley & Lardner LLP; Sunit Talapatra

(57) ABSTRACT

A method is described for using ROR gamma t or ROR alpha to diagnose acne and/or to screen inhibitors of Th17 differentiation. Specifically described, are methods of inhibiting ROR gamma t or ROR alpha and use of the screened inhibitors in acne treatment.

15 Claims, 1 Drawing Sheet

(56) References Cited

OTHER PUBLICATIONS

Figure 1:

Milner, et al., "Impaired TH17 cell differentiation in subjects with autosomal dominant hyper-IgE syndrome," Nature, vol. 452, No. 7188, Mar. 12, 2008, pp. 773-776.
Trivedi, et al., "Gene Array Expression Profiling in Acne Lesions Reveals Marked Upregulation of Genes Involved in Inflammation and Matrix Remodeling," Journal of Investigative Dermatology, Nature Publishing Group, vol. 126, No. 5, May 1, 2006, pp. 1071-1079.
Zhou et al., "IL-6 programs TH-17 cell differentiation by promoting sequential engagement of the IL-21 and IL-23 pathways," Nature Immunology, vol. 8, No. 9, Jun. 20, 2007, pp. 967-974.
Doe, et al. "Expression of the T Helper 17-Associated Cytokines IL-17A and IL-17F in Asthma and COPD", Original Research, vol. 138, No. 5, Nov. 1, 2010, pp. 1140-1147.
Oeff, et al., Dermatology, vol. 213, p. 266 (2006).
Wolk, et al., "Deficiency of IL-22 contributes to a chronic inflammatory disease: pathogenic mechanisms in acne Inversa," J. Immunol., v. 186, pp. 1228-1239; (2011; e-published only Dec. 8, 2010).
Huh, et al., "Digoxin and its derivatives suppress TH17 cell differentiation by antagonizing RORγt activity," Nature, Apr. 28, 2011; 472(7344); pp. 486-490.
Kim et al., "Review of the innate immune response in acne vulgaris: activation of the toll-like receptor 2 in acne triggers inflammatory cytokine responses," Dermatology, 2005, vol. 211, pp. 193-198.
Dispenza, et al., "Systemic isotretinoin treatment modulates patients' immune response to P. acnes," J. Immunol., Apr. 2011, vol. 186, No. 1001, Abstract No. 111.23 (meeting Abstract Supplement).
Experimental Dermatology, vol. 20, p. 169.
Ivanov et al., "The orphan nuclear receptor RORgammat directs the differentiation program of proinflammatory IL-17 T helper cells," Cell 126(9), 2006, pp. 1121-1133.
Korn et al., "IL-17 and Th17 Cells," Annu. Rev. Immunol. 2009, pp. 485-517.
Kurokawa et al., "New developments in our understanding of acne pathogenesis and treatment", John Wiley & Sons A/S, vol. 18, 2009 pp. 821-832.
Leppkes M et al, "S1701 A Crucial Role of Rorgamma Expressing TH17 Cells in Chronic Intestinal Inflammation", Gastroenterology, Elsevier, Philadelphia, PA, vol. 134, No. 4, ISSN 0016-5085, (Apr. 1, 2008), p. A-253 DOI: http://dx.doi.org/10.1016/S0016-5085(08)61172-5.
Leppkes M et al., "RORgamma-Expressing Th17 Cells Induce Murine Chronic Intestinal Inflammation via Redundant Effects of IL-17A and IL-17F", Gastroenterology, Elsevier, Philadelphia, PA, vol. 136, No. 1, ISSN 0016-5085, (Jan. 1, 2009), pp. 257-267 DOI: http://dx.doi.org/10.1053/j.gastro.2008.10.0.
Martinez et al., "BATF: Bringing (in) Another Th17-regulating Factor," Journal of Molecular Cell Buology, vol. 1, 2009, pp. 66-68.
Search Report and Written Opinion issued in Brazilian Patent Application No. 112013033617-0 dated Feb. 11, 2020 (5 pages).
Simon et al., "using human in vivo AHR Activation as a Functional Dose Metric for Risk Assessment Based o Chloracne , Effects in Keratinocytes and Background CYP Induction," Organohalogen Compounds, vol. 72, 2010, pp. 582-585.
Wang et al., "5-Aminolevulinic acid-photodynamic therapy in the control of P. acnes-affected golden hamster sebaceous patches," Linchuang Pifuke Zazhi, vol. 39, No. 7, 2010, pp. 419-419.
Alestas et al., "Enzymes involved in the biosynthesis of leukotriene $B_4$ and prostaglandin $E_2$ are active in sebaceous glands," J. Mol. Med., vol. 84, pp. 75-87, (2006).
Bhatia et al., "Propionibacterium Acnes and Chronic Diseases," The Infectious Etiology of Chronic Diseases—NCBI Bookshelf; (2004).
International Search Report and Written Opinion issued in International Application No. PCT/EP2012/062258, dated Aug. 16, 2012.
International Preliminary Report on Patentability issued in International Application No. PCT/EP2012/062258, dated Jan. 7, 2014.
Perona-Wright et al., "A Pivotal Role for CD40-Mediated IL-6 Production by Dendritic Cells during IL-17 Induction In Vivo"; The Journal of Immunology, vol. 182, pp. 2808-2815; (2009).
Solt et al., "Suppression of $T_H17$ differentiation and autoimmunity by a synthetic ROR ligand"; Nature, vol. 472, No. 7344, pp. 491-494; Apr. 28, 2011.

\* cited by examiner

TH17 DIFFERENTIATION MARKERS FOR ACNE AND USES THEREOF

CROSS-REFERENCE TO PRIOR APPLICATIONS

This application is a divisional of U.S. application Ser. No. 14/129,733, filed Apr. 3, 2014, which is a National Stage of PCT/EP2012/062257, filed Jun. 25, 2012, and designating the United States (published in English on Jan. 3, 2013, as WO 2013/000869 A1), which claims priority under 35 U.S.C. § 119 to U.S. Provisional Patent Application 61/501,363, filed Jun. 27, 2011, each hereby expressly incorporated by reference in its entirety and each assigned to the assignee hereof.

The invention is related to a novel characterization process of acne by identifying for the first time in the inflammatory process the involvement of Th17 cells, and to the therapeutic applications targeting the function of Th17 cells in acne.

More specifically, the invention provides the use of ROR gamma t (also known as RAR-related orphan receptor C or retinoic acid-related orphan receptor (ROR)gamma]t or ROR C variant 2 or RORγ2)), or ROR alpha (also called RORA or RAR-related orphan receptor A), and their use to diagnose acne and/or to screen inhibitors of Th17 differentiation, notably in inhibiting ROR gamma t or ROR alpha and the use of these screened inhibitors in acne treatment.

Acne is the most common skin condition affecting millions of people worldwide. Patients with severe acne frequently face significant psychological and emotional problems due to the scarring associated with the disease. The pathogenesis of acne vulgaris is complex and incompletely understood.

Inflammation is one of the key components of the pathogenesis of acne. An immunological reaction to the gram-positive microbe *P. acnes* may play a major role in the initiation of the inflammatory reaction (De Young L M, Young J M, Ballaron S J, Spires D A, Puhvel S M. Intradermal injection of *Propionibacterium acnes*: a model of inflammation relevant to acne. J Invest Dermatol. 1984 November; 83(5):394-8, Jappe U, Ingham E, Henwood J, Holland K T. *Propionibacterium acnes* and inflammation in acne; *P. acnes* has T-cell mitogenic activity. Br J Dermatol. 2002 February; 146(2):202-9). Recently published studies also implicate Toll Like receptor 2 (TLR-2) in inflammatory acne (Fathy A, Mohamed R W, Ismael N A, El-Akhras M A. Expression of toll-like receptor 2 on peripheral blood monocytes of patients with inflammatory and noninflammatory acne vulgaris. Egypt J Immunol. 2009; 16(1):127-34; Nagy I, Pivarcsi A, Koreck A, Széll M, Urbán E, Kemény L. Distinct strains of *Propionibacterium acnes* induce selective human beta-defensin-2 and interleukin-8 expression in human keratinocytes through toll-like receptors. J Invest Dermatol. 2005 May; 124(5):931-8).

Recent reports demonstrate that the skin expresses various antimicrobial peptides in response to the proliferation of pathogens as part of cutaneous innate immunity (Braff M H, Bardan A, Nizet V, Gallo R L. Cutaneous defense mechanisms by antimicrobial peptides. J Invest Dermatol. 2005 July; 125(1):9-13; Schröder J M. Epithelial antimicrobial peptides: local innate defense effector molecules]. Ann Dermatol Venereol. 2004 April; 131(4):411-6; Selsted M E, Ouellette A J. Mammalian defensins in the antimicrobial immune response. Nat Immunol. 2005 June; 6(6):551-7). Important amongst this group of anti-microbial agents include members of the human β defensin family and granulysin-derived peptides (Deng et al, 2005; Harder et al, 2004; McInturff et al, 2005). Human β defensin-1 and 2 (HBD-1 and HBD-2) are expressed in the pilosebaceous unit and their expression is upregulated in acne lesions (Chronnell et al, 2001). Recent studies have also discovered that select strains of *P. acnes* can activate HBD-2 through TLRs further confirming the importance of these peptides in inflammatory acne (Nagy I, Pivarcsi A, Koreck A, Széll M, Urbán E, Kemény L. Distinct strains of *Propionibacterium acnes* induce selective human beta-defensin-2 and interleukin-8 expression in human keratinocytes through toll-like receptors. J Invest Dermatol. 2005 May; 124(5):931-8).

For the first time, the applicant proposes with experimental evidences to target a novel inflammatory process, the Th-17 cells differentiation for treating and/or diagnosing acne.

Thus, the invention is relating to the use of the DNA or the mRNA encoding ROR gamma t, and also the corresponding proteins, as markers for acne; as well as the use of the DNA or the mRNA encoding ROR alpha, and also the corresponding proteins, as markers for acne. The invention is also relating to the use of at least one of the proposed markers of the invention and/or at least one of the markers chosen from IL-6, IL-17A, IL-17F, IL-21, IL-22, IL-23 A, IL-26, CCL20, as markers for acne is also encompassed in the scope of the invention.

The invention provides a method for the diagnosis of acne, comprising the following steps:
a) detecting the level of expression of at least one of the proposed markers of the invention (ROR gamma t or ROR alpha), and/or at least one of the markers chosen from IL-17A, IL-17F, IL-22, CCL20 in a sample taken from an individual,
b) detecting the level of expression of at least one of the proposed markers of the invention, and/or at least one of the markers chosen from IL-17A, IL-17F, IL-22, CCL20 in a sample taken from a healthy individual,
c) comparing the difference in level of expression of at least one marker and for which the level of expression is significantly higher in the individual than the level of expression in the healthy individual;
d) the overexpression of at least one of the markers of step c) being an indicator of acne, thus diagnosing acne.

The invention provides also a method for the diagnosis of acne that can also comprise the following steps:
a) detecting the level of expression of at least one of the proposed markers of the invention in a sample taken from an individual,
b) detecting the level of expression of at least one of the proposed markers of the invention in a sample taken from a healthy individual,
c) comparing the difference in level of expression of at least one marker and for which the level of expression is significantly higher in the individual than the level of expression in the healthy individual;
d) the overexpression of at least one of the markers of step c) being an indicator of acne, thus diagnosing acne.

The invention provides a method for monitoring the progression of acne, comprising the following steps:
a) taking a biological sample from the individual,
b) analysing the level of expression of at least one of the proposed markers, and/or at least one of the markers chosen from IL-6, IL-17A, IL-17F, IL-22, CCL20 in a sample taken and in which a variation in the expression of at least one of the markers is an indicator of the progression of acne. Progression of acne may be from a predominantly comedonal to a more inflammatory dominated state, it may also mean progression towards specific acne subtypes, like nodulocystic acne or acne conglobata for example. Progression might also occur in the other direction, from a more severe to a less severe form of acne.

The invention provides also a method for monitoring the efficacy of a treatment intended for treating acne, comprising the following steps:
a) administering the desired treatment to the individual identified as having one or more of the symptoms of acne,
b) taking a biological sample from the individual,
c) analysing the level of expression of at least one of the proposed markers of the invention and/or at least one of the markers chosen from IL-17A, IL-17F, IL-22, CCL20, in which a variation in the expression of at least one of the markers is an indicator in the treatment of acne.

The invention relates to an in vitro screening method of Th-cells differentiation inhibitors for treating acne, comprising determining the capacity of said candidate to inhibit or down regulate expression or biological activity of one of the proposed markers (RORgamma t or RORalpha) of the invention.

More specifically, the invention relates to an in vitro screening method of Th17 cells differentiation inhibitors for drug candidates, comprising the following steps:
a) Collecting at least two biological samples: one mimics the acne lesion, and one mimics the healthy condition;
b) Contacting at least one sample or a mixture of samples with one or more drug candidates to be tested;
c) Detecting the expression or the biological function of at least one of the proposed markers, and/or at least one of the expression markers selected from: IL-17A, IL-17F, IL-22, CCL20 in the biological samples or mixture obtained in b);
d) Selecting drug candidates which are capable of inhibiting the expression or the biological function of at least one of the proposed markers, and/or the expression of at least one of the expression markers selected from IL-17A, IL-17F, IL-22, CCL20 measured in said samples or mixtures obtained in b) and comparing the levels with a sample not mixed with the drug candidate(s).

In another embodiment, the invention provides an in vitro screening method of Th17 cells inhibitors for drug candidate, comprising the following steps:
a) Collecting at least two biological samples: one mimics the acne lesion, and one mimics the healthy condition;
b) Contacting at least one sample or a mixture of samples with one or more drug candidates to be tested;
c) Detecting the expression or the biological function of at least one of the proposed markers in the biological samples or mixture obtained in step b);
d) Selecting drug candidates which are capable of inhibiting expression or biological function of at least one chosen from the proposed markers measured in said samples or mixture obtained in step b) and comparing the levels with a sample not mixed with the drug candidate.

The invention relates also to the use of inhibitors identified by screening methods as defined above for the preparation of a composition for treating acne and/or acne associated disorders. More specifically, the invention encompasses the use of inhibitors of the proposed markers identified by screening methods for the preparation of a composition for treating acne or acne associated disorders such as N-(2,2,2-trifluoroethyl)-N-[4-[2,2,2-trifluoro-1-hydroxy-1-(trifluoromethyl)ethyl]phenyl]-benzenesulfonamide, 2 oxysterol (oxygenated sterols), especially 24S-hydroxycholesterol 24(S), 25-epoxycholesterol and 7-oxygenated sterols, Methyl 2-cyano-3,12-dioxooleana-1,9(11)dien-28-oate or Bardoxolone methyl, -(8S,9R,10R,13R,14S,16R,17R)-17-[(E,2R)-2, 6-dihydroxy-6-methyl-3-oxohept-4-en-2-yl]-2,16-dihydroxy-4,4,9,13,14-pentamethyl-8,10,12,15,16, 17-hexahydro-7H-cyclopenta[a]phenanthrene-3,11-dione, 5-(4-chlorophenyl)-6-ethylpyrimidine-2,4-diamine, gamma-D-glutamyl-L-tryptophan, 8-hydroxy-3-methyl-3,4-dihydro-2H-benzo[a]anthracene-1,7,12-trione, 5,7-dihydroxy-2-(4-hydroxyphenyl)-4-oxo-4H-chromen-3-olate, methyl-N-[4-(trifluoromethyl)phenyl]-1,2-oxazole-4-carboxamide or Leflunomide, N-[(E)-(3-methylphenyl)methylideneamino]-6-morpholin-4-yl-2-(2-pyridin-2-ylethoxy)pyrimidin-4-amine.

DETAILED DESCRIPTION

Indeed, Th17 cells, a distinct Th lineage originally from the differentiation of naïve CD4+ T cells, provide immunity against a variety of extracellular pathogens, including bacteria and fungi. Interestingly, although *P. acnes* is a commensal bacteria present in healthy human skin, it has been regarded as one of the pathogenetic factors in acne vulgaris. However, it is still not clear whether *P. acnes* is indeed a causal agent in the development of non-inflamed and inflamed acne lesions (Shaheen B, Gonzalez M. *A microbial aetiology of acne-what is the evidence?* Br J Dermatol. 2011 Apr. 18).

Th17 cells have also been implicated in a variety of inflammatory and autoimmune disorders, such as psoriasis, rheumatoid arthritis and multiple sclerosis (Peck A, Mellins E D. *Precarious balance: Th17 cells in host defense*. Infect Immun. 2010 January; 78(1):32-8).

At molecular level, Th17 cells are characterized by the production of a distinct profile of effector cytokines, IL-17A, IL-17F, IL-26, IL-22, IL-21 and TNFα and depend upon IL-23 for their development, survival and proliferation. These cytokines activate different type of cells, such as keratinocytes, leading to their hyperproliferation and further production of proinflammatory cytokines, chemokines and antimicrobial peptides, which in turn recruit and activate other immune cells in the inflamed skin, leading to amplification of the inflammatory response. Moreover, IL-17A, and IL-17F leading to an autocrine regulation of IL-17 production which serves to promote and sustain Th17 cells differentiation (Wei et al. 2007, J Biol. Chem., September 20). Il 17 is also responsible for the upregulation of CCL2O, the ligand of a characterized receptor of the TH17 cells in stromal cells, allowing the attraction of additional Th17 cells into inflamed tissue.

The signalling pathways of the naive CD4 T cell differentiation into Th17 cells required TGFb-1 either in combination with IL-21, with IL-1b and IL-23 or with IL-1b, IL-23, and IL-6, and lead to the expression of retinoid-related orphan receptor (RORC) and retinoid acid-related orphan receptor alpha (RORA), which are two transcription factors that promote TH17 differentiation and substantially upregulate IL-17A and IL-17F expression (Chung Y et al. Critical regulation of early Th17 cell differentiation by interleukin-1 signaling. Immunity 2009; 30:576-87, Veldhoen M, Hocking R J, Atkins C J, Locksley R M, Stockinger B. and Immunity 2006 February; 24(2):179-89).

For the following, "Th-17 differentiation profile molecules" refers to the biological molecules that characterize the Th17 cell differentiation that is to say the cytokines and/or factors of whom depends the differentiation from naïve T cells to Th-17 cells, in other words IL-6, IL-26, IL-23 and/or which are produced by TH17 cells (IL-17A, IL-17F, IL-21, IL-22, IL-26, TNF alpha, CCL20), and/or also receptors expressed by TH17 cells (CCR6, IL-23R).

Animal experiments place mROR-yt (the mouse ortholog of human ROR gamma t) in the rank of a master regulator of Th-17 differentiation. ROR gamma t deficiency in mice results in diminished Th17 activity and severely reduced expression of IL-17 (Ivanov I I, McKenzie B S, Zhou L, Tadokoro C E, Lepelley A, Lafaille J J, Cua D J, Littman D R. The orphan nuclear receptor ROR gamma t directs the differentiation program of proinflammatory IL-17+ T helper cells. Cell. 2006 Sep. 22; 126(6):1121-33).

The present invention provides ROR gamma t or ROR alpha, crucial actors of Th17 cell differentiation, as novel markers for characterizing acne with the examples which follow.

In particular embodiment, the invention provides the use of the DNA or the mRNA encoding ROR gamma t and also the corresponding proteins, as markers for acne.

In particular embodiment, the invention provides the use of the DNA or the mRNA encoding ROR alpha and also the corresponding proteins, as markers for acne.

In another embodiment, the invention provides the use of at least one of the proposed markers and/or at least one of the markers selected from the following list: IL-6, IL-17A, IL-17F, IL-21, IL-22, IL-23 A, IL-26, TNF alpha or CCL20 as markers for acne.

In another embodiment, the invention provides the used of at least one of the proposed markers and/or at least one of the markers selected from the following list: IL-6, IL-17A, IL-17F, IL-22, CCL20, as markers for acne.

For the purpose of the present invention, the term "marker" or "biological marker" denotes a biological marker associated with the presence or with the absence of a particular pathological state. The biological markers are in particular proteins, mRNAs or DNAs.

For more clarity, the following definitions are used: The term "Proposed markers" means ROR gamma t and/or ROR alpha. "ROR gamma t", means either the expression product of RORC variant 2, i.e ROR gamma mRNA or protein or the RORC gene itself. In analogy, "ROR alpha" means either the expression product of the RORA gene, i.e ROR alpha mRNA or protein or the RORA gene itself.

The term "level of expression" or "expression" means the level of mRNAs or proteins encoded by the gene marker.

The expression level analysis or detection can be performed by any suitable method, known to those skilled in the art, such as western blotting, IHC, mass spectrometry (Maldi-TOF and LC/MS analyses), radioimmunoassay (RIA), Elisa or any other method known to those skilled in the art or else by assaying the mRNA according to the methods customarily known to those skilled in the art. The techniques based on the hybridization of mRNA with specific nucleotide probes are the most customary (Northern blotting, RT-PCR (Reverse Transcriptase Polymerase Chain Reaction), quantitative RT-PCR (qRT-PCR), RNase protection).

In one embodiment, the invention related to a method for the diagnosis of acne, comprises the following steps:
  a) detecting the level of expression of at least one of the proposed above markers, and/or at least one of the markers chosen from IL-6, IL-17A, IL-17F, IL-22, CCL20 in a sample taken from an individual,
  b) detecting the level of expression of and at least one of the above markers, and/or at least one of the markers chosen from IL-6, IL-17A, IL-17F, IL-22, CCL20 in a sample taken from a healthy individual,
  c) comparing the difference in level of expression of at least one marker and for which the level of expression is significantly higher in the sample taken from the individual than the level of expression in the healthy individual;
  d) the overexpression of at least one of the markers of step c) being an indicator of acne, thus diagnosing acne.

The method for the diagnosis of acne can also comprise the following steps:
  a) detecting the level of expression of at least one of the proposed markers in a sample taken from an individual,
  b) detecting the level of expression of at least one of the proposed markers in a sample taken from a normal individual,
  c) comparing the difference in level of expression of at least one marker and for which the level of expression is significantly higher in the sample of the individual than the level of expression in the healthy individual;
  d) the overexpression of at least one of the markers of step c) being an indicator of acne, thus diagnosing acne.

According to another aspect, the invention is related to a method for monitoring the progression or variation of acne, comprising the following steps:
  a) taking a biological sample from the individual,
  b) analysing the level of expression of at least one of the proposed markers, and/or at least one of the markers chosen from IL-6, IL-17A, IL-17F, IL-22, CCL20 in a sample taken and in which a variation in the expression of at least one of the markers is an indicator of the progression of acne. Thus, the invention relates also to a method for the prognosis of the progression or variation of acne.

According to another aspect the invention is related to a method for monitoring the efficacy of a treatment intended for treating acne, comprising the following steps:
  a) administering the desired treatment to the individual identified as having one or more of the symptoms of acne,
  b) taking a biological sample from the individual,
  c) analysing the level of expression of at least one of the proposed markers and/or one of the other markers chosen from 116, IL-17A, IL-17F, IL-22, CCL20, in the sample taken in b), according to any suitable technique known to those skilled in the art, in which a variation in the expression of at least one of the markers is an indicator in the treatment of acne. Preferably, the expression of at least one of the above mentioned markers decreases or moves closer to the level of expression known for a healthy individual.

The expression "overexpression of one of the factors or markers" is intended to mean a level of expression increased by at least 50%, and preferably by at least 100%, and even more preferably by at least 200%, or expressed differently with equivalent significance, by at least a factor of 2, or at least twice as high as the level in a normal individual; which demonstrates overall an overexpression of the chemokines, the cytokines and the receptors mentioned above, thus representing markers characteristic of acne.

In the context of the invention, the biological sample corresponds to any type of sample taken from an individual, and can be a tissue sample or a fluid sample, such as blood, lymph or interstitial fluid.

According to one particular and preferred embodiment, the sample is a biopsy of varying size (preferably from 1 to 6 mm in diameter), or a skin sample taken by means of tape stripping, such as with D-Squames, according to the method described in Wong R et al., "Analysis of RNA recovery and gene expression in the epidermis using non-invasive tape stripping"; J Dermatol Sci. 2006 November; 44(2):81-92; or in Benson N R, et al., "An analysis of select pathogenic messages in lesional and non-lesional psoriatic skin using non-invasive tape harvesting". J Invest Dermatol. 2006 October; 126(10): 2234-41; or else in Wong R et al., "Use of RT-PCR and DNA microarrays to characterize RNA recovered by non-invasive tape harvesting of normal and inflamed skin". J Invest Dermatol. 2004 July; 123(1):159-67. According to the principle of tape stripping, the product used comprises a flexible translucent polymer support and an adhesive. The product is applied repeatedly to the skin of the patient, preferably until loss of adhesion. The sample obtained relates only to the content of the outermost layers of the epidermis. A method for analysing a protein content obtained in particular according to this sampling method is described in Patent Application WO2009/068825 (Galderma R&D) in order to monitor markers specific for a pathological skin condition and to orient the diagnosis. Since this method is rapid, non-invasive and relatively inexpensive for detecting the presence of, the absence of or the variation in certain proteomic markers, it is particularly preferred. This method is in particular characterized by mass spectrometry detection, ELISA or any other method known to the expert skilled in the art of protein quantification. Quantification is performed in the skin sample obtained on the flexible and adhesive support in order to detect at least one protein of which the presence, the absence or the variation in amount or in concentration compared with a standard value is associated with the presence, with the progression or with the absence of a particular pathological skin condition.

Another embodiment of the present invention is an in vitro screening method of Th17 cell differentiation candidate inhibitors, comprising determining the capacity of said candidate to inhibit and/or down regulate the expression or the biological activity or the biological function, including the transactivation properties, of at least one of the proposed markers (RORgamma t or RORalpha) of the invention. The identified candidate will influence the biological function of a given marker or a biological process modulated by the marker. For example, the inhibition of ROR gamma t and/or ROR alpha by a candidate may affect the biological function of ROR gamma t, including the induction of the Th17 cell differentiation as well as the function of Th17 cells.

For screening purposes, the biological samples consist of transfected cells containing reporter genes operating under the control of a promoter (totally or partially) controlling the expression of an above mentioned gene. Alternatively, the promoter may be, at least in part, synthetically assembled and contain ROR-responsive elements. The ability of a compound to modulate the function of the proposed markers, is evaluated by analyzing the expression of the reporter gene.

The transfected cells may further be engineered to express at least one of the proposed markers.

The reporter gene may encode an enzyme that with its corresponding substrate, provides coloured product(s) such as CAT (chloramphenicol acetyltransferase), GAL (beta galactosidase), or GUS (beta glucuronidase). It might be either luciferase or GFP (Green Fluorescent Protein).

Reporter gene protein dosage or its activity is typically assessed by colourimetric, fluorometric or chemoluminescence methods.

According to a further embodiment of the invention, biological samples are cells expressing the gene of interest and the step c) above consists to measure the activity of the gene product.

In another embodiment, the invention is related to the use of identified inhibitors/antagonists/inverse agonists with the described screening methods for the preparation of a composition for treating acne and/or acne associated disorders.

In particular, the inhibitors/antagonists/inverse agonists of gamma t or ROR alpha could be selected from the following list:

N-(2,2,2-trifluoroethyl)-N-[4-[2,2,2-trifluoro-1-hydroxy-1-(trifluoromethyl)ethyl]phenyl]-benzenesulfonamide; this compound is a novel retinoic acid receptor-related orphan receptor-alpha/gamma inverse agonist. (Mol Pharmacol. 2010 February; 77(2):228-36))

2 oxysterol (oxygenated sterols), especially 24S-hydroxycholesterol 24(S), 25-epoxycholesterol and 7-oxygenated sterols [a second class of nuclear receptors for oxysterols: Regulation of RORalpha and RORgamma activity by 24S-hydroxycholesterol (cerebrosterol)—Wang Y et al. Biochim Biophys Acta. 2010 August; 1801(8):917-23. Epub 2010 Mar. 6]; Wang Y et al. *Modulation of retinoic acid receptor-related orphan receptor alpha and gamma activity by 7-oxygenated sterol ligands*. J Biol Chem. 2010 Feb. 12; 285(7): 5013-25))

Methyl2-cyano-3,12-dioxooleana-1,9(11)dien-28-oate or Bardoxolone methyl (also known as "RTA 402" and "CDDO-methyl ester).

(8S,9R,10R,13R,14S,16R,17R)-17-[(E,2R)-2, 6-dihydroxy-6-methyl-3-oxohept-4-en-2-yl]-2,16-dihydroxy-4,4,9,13, 14-pentamethyl-8,10,12,15,16, 17-hexahydro-7H-cyclopenta[a]phenanthrene-3,11-dione or SI-124 (Blaskovich M A, Sun J, Cantor A et al. Discovery of JS-124 (cucurbitacin I), a selective Janus Kinase/Signal Transducer and Activator of Transcription 2 signaling pathway inhibitor with potent antitumor activity against human and murine cancer cells in mice Cancer Res 2003; 63: 1270-1279)

Pyrimethamine: -5-(4-chlorophenyl)-6-ethylpyrimidine-2,4-diamine or Pyrimethamine (Dariprim)(WO/2008/156644)

gamma-D-glutamyl-L-tryptophan or SCV-07 (SciClone Pharmaceuticals)(Nagabhushanam V, Subbarao K, Ramachandran M et al Inhibition of STAT3 driven gene expression in melanoma cells by SCV-07 J Clin Oncol 2008; 26 (May 20, suppl): 14619)

8-hydroxy-3-methyl-3,4-dihydro-2H-benzo[a]anthracene-1,7,12-trione or STA-21 (Song H, Wang R, Wang S et al. A low-molecular-weight compound discovered through virtual database screening inhibits Stat3 function in breast cancer cells PNAS 2005; 102: 4700-4705 natural flavonol: such as 5,7-dihydroxy-2-(4-hydroxyphenyl)-4-oxo-4H-chromen-3-olate or Kaempferol (Bruno R D, Njar V C. Targeting cytochrome P450 enzymes: *a new approach in anti-cancer drug development*. Bioorg Med Chem. 2007 Aug. 1; 15(15):5047-60. Epub 2007 May 23).

methyl-N-[4-(trifluoromethyl)phenyl]-1,2-oxazole-4-carboxamide or Leflunomide (O'Donnell E F, Saili K S, Koch D C, Kopparapu P R, Farrer D, Bisson W H, Mathew L K, Sengupta S, Kerkvliet N I, Tanguay R L, Kolluri S K. The anti-inflammatory drug leflunomide is an agonist of the aryl hydrocarbon receptor. PLoS One. 2010 Oct. 1;5(10).

N-[(E)-(3-methylphenyl)methylideneamino]-6-morpholin-4-yl-2-(2-pyridin-2-ylethoxy)pyrimidin-4-amine or STA 5326 (Apilimod Synta pharmaceuticals) Wada et al: Selective abrogation of Th1 response by STA-5326, a potent IL-12/IL-23 inhibitor. Blood, 2007, 109(3), 1156-1164. Wada et al: IL-12/IL-23 inhibitors:

a promising approach to the treatment of inflammatory disorders. Drugs Fut. 2008, 33(1), 49-63

[(3S,5R,8R,9S,10S,12R,13S,14S)-3-[(2S,4S,5R,6R)-5-[(2S,4S,5R,6R)-5-[(2S,4S,5R,6R)-4,5-dihydroxy-6-methyl-oxan-2-yl]oxy-4-hydroxy-6-methyl-oxan-2-yl]oxy-4-hydroxy-6-methyl-oxan-2-yl]oxy-12,14-dihydroxy-10,13-dimethyl-1, 2,3,4,5,6,7,8,9,11,12,15,16,17-tetra decahydrocyclopenta[a]phenanthren-17-yl]-5H-furan-2-one or Digoxin and its derivatives.

In another aspect, inhibitors might be either a polypeptide, a DNA or an antisense RNA, an si-RNA or a PNA ("Peptide nucleic acid", i-e with a polypeptidic chain substituted by purine and pyrimidine bases and having a DNA-like structure for hybridization to this latter).

The modulator might be an antibody and preferably a monoclonal antibody. Advantageously, the monoclonal antibody is administered to a patient in a sufficient quantity so as the measure a plasmatic concentration is from about 0.01 µg/ml to about 100 µg/ml, preferred from about 1 µg/ml to about 5 µg/ml.

The invention is intended for treating acne. By acne it is understood, all acne forms especially simple acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne and medication-related acne and also more largely, acne associated disorders (e.g. hyperseborrhoea).

The example which follows illustrates the invention without limiting the scope thereof.

Table 1: mRNA expression measured by Affymetrix Technology. Analysis of Th17 differentiation profile molecules IL-17A, IL-17F, IL-26, IL-6 and proposed markers RORA and RORC, as well as IL-5, IL-4 IL-13 typically considered as Th2 cytokines.

Table 2: mRNA expression measured by qRT-PCR (TaqMan low density Array technology). Analysis of the expression of Th17 differentiation profile molecules IL-6, IL-17, IL-22, IL-23, CCL20, IL-6 and RORC, one of the proposed markers, as well as IL-5, IL-4 and IL-13 typically considered as Th2 cytokines.

Table 3: Protein expression of Th17 differentiation profile molecules (Luminex assay). Analysis of IL-6, IL-17A, IL-17F, IL-21, IL-22, IL-23a, CCL20 and TNF alpha, as well as IL-5, IL-4 and IL-13 typically considered as Th2 cytokines.

FIG. 1: Acne lesion: T lymphocyte immunohistochemical detection (CD3 alone)

Figure 2:

FIG. 2: Acne lesion: IL-17 expression in T lymphocytes (CD3/IL 17 co-localisation)

EXAMPLE 1: MODULATION OF THE TH17 MOLECULAR PROFILE IN THE LESIONAL SKIN OF PATIENTS SUFFERING FROM ACNE COMPARED WITH NON-LESIONAL SKIN OF THESE PATIENTS: ANALYSIS OF THE EXPRESSION OF IL-6, IL-17A, IL-17F, IL-21, IL-22, IL-23A, IL-26, TNF ALPHA, CCL20 AND THE PROPOSED MARKERS RORA AND RORC

Patient Selection and Tissue Biopsies:

Skin biopsies of acne patients were obtained from an inflammatory papule and from non lesional skin in 12 patients with acne, in accordance with good clinical practice. (The clinical description of acne subtypes was carried out according to the classification of Wilkin et al., 2002, J. Am. Acad. Dermatol. Vol 46, pages 584-587.)

To evaluate a change in the expression level of the genes, the expression levels in lesional skin are compared with the expression levels in non-lesional skin of the same subjects (n=12).

mRNA Extraction, Labelling and Hybridization to Probe Arrays:

The mRNA was isolated from skin using the RNeasy extraction kit (Quigen Inc., Valencia, Calif.) and quality was evaluated using a 2100 Bioanalyser of Agilent. The mRNA expression was evaluated by a Gene Chip IVT labelling kit after the generation of double-stranded cDNA (i.e in vitro transcription process) using T7-oligo primer and the one cycle cDNA synthesis kit of Affymetrix. RNA was ethanol precipitated to concentrate the sample and then quantified using a spectrophotometer. Approximately 200 ng of total RNA of good quality [RNA indication number (RIN)≥7] from each sample was used to generate double-stranded cDNA using a T7-oligo (dt) primer (one cycle cDNA synthesis kit, Affymetrix). Biotinylated cRNA, produced through in vitro transcription (Gene Chip IVT labelling kit, Affymetrix) was fragmented and hybridised to an Affymetrix human U133A 2.0 plus microarray. The arrays were processed on a Gene Chip Fluidics Station 450 and scanned on an Affymetrix Gene Chip Scanner (Santa Clara, Calif.).

Statistical Analysis of mRNA Expression Based on Affymetrix Gene Chips:

The expression data from Affymetrix Gene Chips are normalized with RMA (Robust Multi-array Analysis) method. The raw intensity values are background corrected, log 2 transformed and then quantile normalized. Next a linear model is fit to the normalized data to obtain an expression measure for each probe set on each array. To identify genes that were significantly modulated in the different Acne subtype samples, one-way ANOVA with Benjamini-Hochberg multiplicity correction was performed using JMP 7.0.1 (SAS Institute) and irMF 3.5 (National Institute of Statistical Sciences, NISS) software.

qRT-PCR Measurement of mRNA expression:

The expression of the Th17 differentiation profile was also measured by qRT-PCR.

In the following table the expression levels are documented using the Mean Ct (Cycle Threshold) of individual genes in non lesional skin and in lesional skin of acne patients. The Ct value is inversely proportional to the quantity of the mRNA of a given gene.

Cytokine Extraction and Assay:

Proteins were extracted from inflammatory papules and non lesional skin in 12 patients with acne. Cytokines were dosed in the protein extracts using Luminex assays (Millipore & Procarta cytokine dosage kits). The cytokine quantities were normalized to the total concentration of protein. Paired P-values were calculated for each cytokine.

The mRNA expression of the Th17 differentiation profile molecules: IL-17A, IL-17F, IL-26, CCL20 and proposed markers ROR A and ROR C were measured using Affymetrix technology (Table 1) and qRT-PCR (Table 2).

The mRNA of specific cytokines IL-17A, IL-17F, IL-22, IL-26 characterizing Th17 cells differentiation measured by Affymetrix (table 1) or qRT-PCR (table 2) techniques are significantly up-regulated in lesional skin. Moreover, in these tables, the mRNA expression of IL5, IL4 and IL13 are not detected or not changed suggesting that the inflammatory response in acne is not driven by Th2 cells.

Table 3 demonstrates an up-regulation of the protein expression level of IL-6, IL-17A, IL-17F, IL-21, IL-22 and TNF alpha in lesional skin in comparison to non-lesional skin.

Thus, these expression differences of cytokines implicated in the Th-17 cell differentiation process demonstrate the interest of inhibiting or targeting Th17 cell differentiation for the treatment or diagnosis of acne.

Surprisingly, the mRNA levels of the transcription factors ROR A and ROR C are slightly decreased in acne, but their expression in human skin was clearly demonstrated. Thus, they are interesting as markers for diagnosing acne and/or screening inhibitors of Th17 cells differentiation. For diagnostic purposes, they can be used alone or in combination with at least one of the Th17 cell differentiation profile molecules mentioned previously.

EXAMPLE 2: IMMUNOHISTOCHEMISTRY ANALYSIS

In normal skin, we observed hardly any lymphocyte infiltrates whereas in biopsies from lesional areas there were found in greater numbers. In this context, IL17 detection using an immunohistochemistry technique was performed in these infiltrates from lesional areas.

A first primary antibody (anti CD3) was used in order to detect the T lymphocytes, followed by a second antibody, specific for IL-17.

These antibodies were respectively revealed with a second antibody combined with a red fluorophore (TRITC) or a green fluorophore (FITC).

The results for CD3 expression are presented in FIG. 1. The positive cells, in black, confirmed that the infiltrate was largely composed of T lymphocytes.

FIG. 2 demonstrates that a subpopulation of CD3 positive T lymphocytes co-expressed IL-17. This positive IL-17 staining suggests the presence of Th17 cells in acne lesions.

TABLE 1

| GENE_SYMBOL | TITLE | Non lesional skin Mean_Expressions | Lesional skin Mean_Expressions | Lesional skin vs non lesional skin Fold Change | Lesional skin vs non lesional skin Adjusted Pvalue |
| --- | --- | --- | --- | --- | --- |
| IL6 | interleukin 6 (interferon, beta 2) | 73 | 340 | 4.7 | 1.3E−03 |
| IL17A | interleukin 17A | 13 | 57 | 4.3 | 7.8E−03 |
| CCL20 | chemokine (C-C motif) ligand 20 | 146 | 482 | 3.3 | 1.6E−03 |
| IL17F | interleukin 17F | 35 | 88 | 2.5 | 1.1E−02 |
| IL26 | interleukin 26 | 24 | 48 | 2.0 | 2.3E−03 |
| RORA | RAR-related orphan receptor A | 9776 | 4542 | −2.2 | 6.0E−04 |
| RORC | RAR-related orphan receptor C | 236 | 106 | −2.2 | 7.0E−04 |
| IL5 | interleukin 5 (colony-stimulating factor, eosinophil) | Not detected | Not detected | | |
| IL4 | interleukin 4 | Not detected | Not detected | | |
| IL13 | interleukin 13 | 78.61 | 79.65 | 1.0 | 8.0E−01 |

TABLE 2

| GENE_SYMBOL | TITLE | Non lesional skin Mean_CT | Lesional skin Mean_CT | Lesional skin vs non lesional skin Fold Change | Lesional skin vs non lesional skin P-value |
| --- | --- | --- | --- | --- | --- |
| IL23A | interleukin 23, alpha subunit p19 | 32.8 | 30.1 | 6.23 | 1.5E−08 |
| IL6 | interleukin 6 (interferon, beta 2) | 30.3 | 27.7 | 6.22 | <0.0001 |
| IL17A | interleukin 17A | 32.3 | 29.9 | 5.55 | <0.0001 |
| IL22 | interleukin 22 | 34.0 | 32.7 | 2.42 | 8.1E−06 |
| CCL20 | chemokine (C-C motif) ligand 20 | 29.2 | 28.0 | 2.35 | 6.8E−10 |
| RORC | RAR-related orphan receptor C | 24.3 | 26.8 | −5.47 | <0.0001 |
| IL5 | interleukin 5 (colony-stimulating factor, eosinophil) | 34.3 | 35.4 | −2.08 | 5.26E−13 |
| IL4 | interleukin 4 | 34.2 | 35.3 | −2.12 | 2.03E−08 |
| IL13 | interleukin 13 | 34.3 | 35.4 | −2.19 | 2.53E−13 |

TABLE 3

| Proteins | LSP | NSP | FoldChange | PValue |
|---|---|---|---|---|
| Interleukin-6 | 16.2 | 1.1 | 15.0 | 0.0005 |
| interleukin-17F | 1.2 | 0.3 | 4.9 | 3.2E−03 |
| Interleukin-21 | 29.1 | 7.5 | 3.9 | 1.1E−02 |
| Interleukin-17A | 4.0 | 1.1 | 3.8 | 0.0081 |
| Interleukin-22 | 14.3 | 4.6 | 3.1 | 3.2E−02 |
| Interleukin-23 subunit alpha | 1.0 | 0.3 | 3.1 | 1.7E−01 |
| C-C motif chemokine 20 | 1.0 | 0.4 | 2.6 | 4.0E−02 |
| Tumor necrosis factor alpha | 2.6 | 1.1 | 2.5 | 0.0182 |
| Interleukin-4 | 4.2 | 1.9 | 2.2 | 0.0052 |
| Interleukin-5 | not detected | not detected | | |
| Interleukin-13 | 3.3 | 2.1 | 1.6 | 0.0678 |

The invention claimed is:

1. A method of treating a human subject for acne, the method comprising:
   (a) obtaining or having obtained a lesional skin sample from the subject;
   (b) detecting or having detected expression of the following in the lesional skin sample:
      (i) at least one first marker comprising DNA encoding ROR gamma t, DNA encoding ROR alpha, mRNA encoding ROR gamma t, mRNA encoding ROR alpha, ROR gamma t, or ROR alpha; and
      (ii) at least one second marker selected from the group consisting of IL-17A, IL-17F, and CCL20;
   (c) detecting or having detected expression of the at least one first marker and the at least one second marker in a non-lesional skin sample from a healthy individual;
   (d) determining or having determined that the lesional skin sample from the subject exhibits expression of the at least one first marker and exhibits increased expression of the at least one second marker as compared to the non-lesional skin sample from the healthy individual; and
   (e) administering to the subject an acne treatment selected from the group consisting of N-(2,2,2-trifluoroethyl)-N-[4-[2,2,2-trifluoro-1-hydroxy-1-(trifluoromethyl) ethyl]phenyl]-benzenesulfonamide; 2-oxygenated sterols; 24S-hydroxycholesterol; 24(S),25-epoxycholesterol; 7-oxygenated sterols; methyl 2-cyano-3,12-dioxooleana-1,9(11)dien-28-oate; bardoxolone methyl, cucurbitacin I; 5-(4-chlorophenyl)-6-ethylpyrimidine-2,4-diamine; gamma-D-glutamyl-L-tryptophan; 8-hydroxy-3-methyl-3,4-dihydro-2H-benzo[a]anthracene-1,7,12-trione; 5,7-dihydroxy-2-(4-hydroxyphenyl)-4-oxo-4H-chromen-3-olate; leflunomide; and N-[(E)-(3-methylphenyl)methylideneamino]-6-morpholin-4-yl-2-(2-pyridin-2-ylethoxy) pyrimidin-4-amine; and combinations thereof.

2. The method of claim 1, wherein the acne is simple acne, comedonic acne, paulopustular acne, papulocomedonic acne, nodulocystic acne, acne conglobate, cheloid acne of the nape of the neck, recurrent military acne, necrotic acne, neonatal acne, occupational acne, acne rosacea, senile acne, solar acne, or medication-related acne.

3. The method of claim 2, wherein the acne is simple acne.

4. The method of claim 1, wherein the expression of the at least one first marker is mRNA encoding ROR gamma t.

5. The method of claim 1, wherein the expression of the at least one first marker is mRNA encoding ROR gamma t and mRNA encoding ROR alpha.

6. The method of claim 1, wherein the expression of the at least one first marker is greater in the non-lesional skin sample from the healthy individual as compared to the lesional skin sample from the subject.

7. The method of claim 1, wherein the lesional skin sample from the subject and/or the non-lesional skin sample from the healthy individual are from the epidermis.

8. The method of claim 7, wherein the lesional skin sample from the subject and/or the non-lesional skin sample from the healthy individual are from the outermost layers of the epidermis.

9. The method of claim 1, wherein the lesional skin sample from the subject and/or the non-lesional skin sample from the healthy individual are collected by tape stripping.

10. The method of claim 1, wherein the increased expression of the at least one second marker is an increase of at least 50%.

11. The method of claim 10, wherein the increased expression of the at least one second marker is an increase of at least 200%.

12. The method of claim 1, wherein the at least one second marker is IL-17A.

13. The method of claim 1, wherein the at least one second marker is IL-17F.

14. The method of claim 1, wherein the at least one second marker is CCL20.

15. The method of claim 1, wherein the at least one first marker is mRNA encoding gamma t and the at least one second marker is IL-17A.

* * * * *